(12) United States Patent
Marks (10) Patent No.: US 8,043,268 B1
(45) Date of Patent: Oct. 25, 2011

(54) SAFETY NEEDLE AND METHOD OF USING SAME

(76) Inventor: Lloyd A. Marks, Westfield, NJ (US)

( * ) Notice: Subject to any disclaimer, the term of this patent is extended or adjusted under 35 U.S.C. 154(b) by 0 days.

(21) Appl. No.: 12/177,545

(22) Filed: Jul. 22, 2008

(51) Int. Cl.
*A61M 5/32* (2006.01)

(52) U.S. Cl. ......... 604/198; 604/110; 604/192; 604/263

(58) Field of Classification Search .................. 604/110, 604/192, 198, 263
See application file for complete search history.

(56) References Cited

U.S. PATENT DOCUMENTS

| | | | |
|---|---|---|---|
| 3,134,380 A | 5/1964 | Armao | |
| 3,840,008 A | 10/1974 | Noiles | |
| 4,139,009 A | 2/1979 | Alvarez | |
| 4,735,618 A | 4/1988 | Hagen | |
| 4,790,828 A | 12/1988 | Dombrowski et al. | |
| 4,867,172 A | 9/1989 | Haber et al. | |
| 4,935,013 A | 6/1990 | Haber et al. | |
| 4,950,250 A | 8/1990 | Haber et al. | |
| 4,998,922 A | 3/1991 | Kuracina et al. | |
| 5,078,697 A | 1/1992 | Rammler | |
| 5,242,417 A | 9/1993 | Paudler | |
| 5,250,031 A | 10/1993 | Kaplan et al. | |
| 5,256,152 A * | 10/1993 | Marks ........................... | 604/198 |
| 5,304,192 A | 4/1994 | Crouse | |
| 5,348,544 A | 9/1994 | Sweeney et al. | |
| 5,531,704 A | 7/1996 | Knotek | |
| 5,538,508 A | 7/1996 | Steyn et al. | |
| 5,713,872 A | 2/1998 | Feuerborn et al. | |
| 5,746,718 A | 5/1998 | Steyn et al. | |
| 5,925,020 A | 7/1999 | Nestell | |
| 6,409,706 B1 | 6/2002 | Loy | |
| 6,918,891 B2 | 7/2005 | Bressler et al. | |
| 6,986,759 B1 * | 1/2006 | Jeremijevic ................... | 604/198 |
| 7,211,069 B2 | 5/2007 | Lehmann et al. | |
| 7,300,423 B2 | 11/2007 | Cocker et al. | |
| 7,320,682 B2 | 1/2008 | Cocker et al. | |
| 2004/0162532 A1 * | 8/2004 | Cocker et al. ................. | 604/264 |
| 2007/0100296 A1 | 5/2007 | Hwang | |

* cited by examiner

*Primary Examiner* — Kevin C Sirmons
*Assistant Examiner* — Edelmira Bosques
(74) *Attorney, Agent, or Firm* — Blank Rome LLP (57) ABSTRACT

A safety hypodermic needle and a method of using the same are disclosed. The safety needle comprises a hypodermic needle and a protective sheath molded of a flexible polymeric material. The protective sheath comprises a needle sleeve with an open central passage which houses the sharp needle point. The needle sleeve is supported on a plurality of inwardly bowed ribs in an unflexed "at rest" condition in which the needle point is retained inside the needle sleeve to prevent inadvertent needle sticks. Levers attached to the ribs are used to move the ribs from their inwardly bowed unflexed "at rest" condition to an outwardly bowed flexed condition to permit the needle to pass through the open central passage of the needle sleeve and into a patient's body. After the needle is removed from the patient's body, the ribs automatically return to the unflexed "at rest" condition without the assistance of any additional biasing or restoring means.

12 Claims, 4 Drawing Sheets

SAFETY NEEDLE AND METHOD OF USING SAME

BACKGROUND OF THE INVENTION

1. Field of the Invention

The present invention relates generally to hypodermic syringes and phlebotomy apparatus and more particularly to a safety hypodermic needle for disposable hypodermic syringes and phlebotomy apparatus and a method of using the safety needle to prevent inadvertent needle sticks or punctures.

2. Description of the Prior Art

Infectious diseases can be transmitted to medical personnel and others by way of inadvertent needle sticks or punctures with an infected needle of a hypodermic syringe or phlebotomy apparatus. Cases have been reported in which human HIV (AIDS) infection and other infectious diseases have been transmitted by accidental or inadvertent needle sticks. A number of devices have been developed for the purpose of preventing such needle sticks.

One prior art device comprises a spring-biased tube located within the lumen of the needle. After the needle has been used, the tube is advanced by the spring beyond the needle bevel point thereby protecting medical and other personnel from an inadvertent needle stick. This device is relatively complex, costly and reduces the effective lumen size of the needle.

Another type of prior art device in more common use employs a protective sheath external to the needle which is retractable to permit insertion of the needle into the body of the patient and is then slidable back over the needle past the needle point as, or after, the needle is withdrawn from the body. In some of this type of prior art protective device, a spring or axially resilient sheath is used to extend the sheath over the needle point upon withdrawal of the needle. Several of these prior art devices use a collapsible sheath formed by a plurality of resilient arms surrounding the needle. The arms are bowable or bendable outwardly away from the needle axis to expose the needle and are movable inwardly toward the needle axis with or without a biasing means to again enclose the needle within the sheath. Some of these devices require a positive step or a specific manual act by the phlebotomist or user to deploy the protective sheath after it is withdrawn from the patient's body. Still other devices are made from a plurality of parts making them more complex to manufacture and thus more costly to the consumer.

One of the primary shortcomings of the prior art devices which use protective sheaths of the foregoing type is that during at least some of the period of time between the preparation of the hypodermic syringe for an injection, or the phlebotomy apparatus for entering a vein, and the discarding of the used needle, inadvertent needle sticks of persons other than the patient are still possible. In some prior art devices, the protective sheath does not cover the needle tip prior to administering the needle to the patient, and in others, the protective sheath does not positively prevent exposure of the needle tip after administering the needle to the patient.

It would be desirable, therefore, to provide a safety hypodermic needle for use with a disposable hypodermic syringe, as well as for use with catheter needles and other types of body-penetrating hypodermic needles, that overcomes the foregoing limitations and shortcomings of the prior art devices, has a minimum number of parts, is economical to manufacture and is easy and convenient to use. In particular, it would be highly desirable and advantageous to provide a safety needle that is operable in its "at rest" state to positively prevent inadvertent exposure of the needle point at all times, both before and after use, and to permit exposure of the needle point for use on a patient only in response to a specific manual action or manipulation of the safety needle components on the part of the user, which may include breaking, rupturing or otherwise disengaging a member that retains the safety needle in its "at rest" safe state.

My prior U.S. Pat. No. 5,256,152, the entire disclosure of which is incorporated herein by reference, efficiently and effectively solves many of the aforementioned problems and shortcomings of other prior art safety devices for hypodermic needles and the like. The present invention provides still further improvements in those other prior art safety devices for hypodermic needles as will be described in detail in the following specification.

SUMMARY OF THE INVENTION

The present invention is directed to improvements in a safety needle and to an improved method of using the safety needle to prevent inadvertent needle sticks. The safety needle of the invention comprises a needle, typically a hollow, hypodermic needle with a sharp bevel point or tip, a support hub into which the needle is inserted and a protective sheath which is fixed at one end to the hub and at least partially encloses the greater part of the longitudinal extent of the needle shaft and completely encloses the needle point in a needle passage until the needle is ready to be inserted in the body. The protective sheath is preferably molded in one piece of a suitable polymeric material, such as polyethylene, polypropylene or the like, and preferably a clear or transparent material. Other manufacturing techniques, such as extrusion, may be employed. The protective sleeve or sheath may also be made of different materials, preferably polymeric materials, and assembled together in its final form. In addition, the protective sheath may be molded or made with regions of different stiffness so that some regions are more or less flexible than others.

The protective sheath has a generally tubular form, preferably with a circular or elliptical cross-section, and comprises a first tubular portion, or mounting sleeve, that is fixed to or over the needle support hub and a second tubular portion or needle sleeve that surrounds and extends slightly beyond the bevel point of the needle tip. The second tubular portion or needle sleeve has a passage, preferably a central passage, through which the needle shaft is adapted to pass. One or a plurality of flexible ribs or arms extends longitudinally between the first and second tubular portions and substantially parallel to the needle shaft. In its "at rest" or initial state or condition, each of the ribs or arms has a curvilinear shape arranged with an outwardly facing concave surface and an inwardly facing convex surface, the at rest, curvilinear-shaped rib or arm being hereinafter variously described as an inwardly bowed rib or arm, an inwardly curved rib or arm, an inwardly directed rib or arm or like terminology. The term "at rest" as used herein to describe the initial, inwardly curved state or condition of the flexible ribs or arms includes an unflexed or relaxed state of the arms requiring no additional component, such as a biasing or restoring means to maintain the arms in such "as rest" state or to return the arms to the "at rest" state.

When a force is applied axially to the free end of the sheath in a direction to axially shorten the sheath, i.e., in a direction to move the first and second tubular portions toward one another, the ribs are constrained by their particular initial inwardly curvilinear shape to flex or bow inwardly toward and in contact with the needle shaft and, in some cases, in contact with each other. When the first and second tubular portions are moved axially toward one another to the maximum extent, the needle tip still remains inside the central passage of the second tubular member. Thus, if an axial compressive force is applied to the protective sheath (for example, as might accidentally occur if a hypodermic syringe to which the needle is attached were dropped or inadvertently brought into contact with the body of the person administering the injection or carrying out the phlebotomy procedure), the needle point cannot extend axially out of the central passage of the second tubular portion to cause an inadvertent needle stick. In the "at rest" or unflexed safe condition of the protective sheath, that is, with no external forces acting on the sheath, the needle bevel point is fully enclosed within the central passage of the second tubular portion thereby effectively protecting against inadvertent needle sticks.

In one embodiment, each rib or arm is provided with an operator element, such as an arm or lever, that when manually operated by the user of the safety needle, flexes or bows its associated rib or arm outwardly away from its inwardly bowed or "at rest" and unflexed initial state. Each rib operator element of this embodiment is preferably molded integrally with its associated rib or arm and is arranged at an angle with respect to the needle shaft axis. One or more of the operator elements or ribs may be provided with a breakaway member that must be broken or otherwise disengaged in order to operate the safety needle.

When it is desired, for instance, according to the method aspects of the invention, to administer an injection with the safety needle of the invention, the user removes the syringe and attached safety needle from its package with the safety needle in its safe or "at rest" state. Assuming the syringe is prefilled, the user first breaks or disengages any breakaway or latch member that positively locks the safety needle in its safe or "at rest" state. The user then manually grasps the one or more operator elements for the rib or ribs and moves, e.g., pivots, the operator elements through a sufficient angle to cause the ribs to bow or flex outwardly away from the needle shaft and move the second tubular member axially toward the first tubular member to expose the needle point from the open end of the central passage. The needle point is then engaged with the skin of the patient and the needle is advanced into the injection site. Once the needle point engages the patient's skin, the rib operator elements may be released by the user.

As the needle continues to penetrate into the patient's body, the second tubular member is axially urged farther toward the first tubular member and the ribs are bowed or flexed outwardly to a greater extent by reason of the axial movement of the second tubular member. After the syringe has been operated to complete the injection, the needle is withdrawn from the patient and the ribs bow or flex inwardly and the protective sheath returns to its unflexed or "at rest" state with the needle point fully enclosed within the central passage of the second tubular member. In this way, a needle which is potentially contaminated with the body fluids of a patient carrying an infectious disease is rendered safe from the standpoint of inadvertent needle sticks. In addition, a broken breakaway or latch member gives a warning indication that a syringe may have been used.

In another embodiment of the invention, the operator element comprises a curved member or ring spanning the ribs adjacent the first tubular portion. When the curved member or ring is manually pressed or forced radially inwardly toward the needle shaft, the ribs flex outwardly as described above.

In other advantageous embodiments of the invention, especially for administering injections with hypodermic syringes, a latching means may be provided for positively and irreversibly latching the protective sheath in the "at rest" condition, that is, with the ribs flexed inwardly and the needle fully enclosed in the central passage after the injection has been administered. Such latching means may comprise a hook on the first tubular member or mounting sleeve that is engaged, either automatically or manually by the user, with at least one rib or operator element after the needle is withdrawn from a patient. With the hook engaged, the operator element cannot without difficulty be operated to expose the needle point. This irreversibly latched condition signifies to medical personnel that the syringe has been used and should be discarded. As used herein, the term "irreversibly" is intended to include latching means that is impossible to unlatch, as well as latching means that cannot be unlatched without some significant difficulty, e.g., by destroying the latch.

Several additional embodiments of the invention are disclosed including an embodiment in which only one of a plurality of ribs or arms is bowed or curved inwardly, the other ribs or arms being bowed or curved outwardly.

The safety needle of the invention can also be used in medical procedures for inserting catheters into blood vessels with a needle, in phlebotomy procedures and in other procedures in which hypodermic needles are used and the danger of inadvertent needle sticks exist.

Although a number of embodiments of the safety needle of the invention are disclosed in the specification and accompanying drawings, it should be understood that, apart from the specific embodiments disclosed herein, this invention is generally applicable to any type of hypodermic needle used to penetrate the body to either introduce a substance into the body or to withdraw a substance from the body, such as blood or other body fluids.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
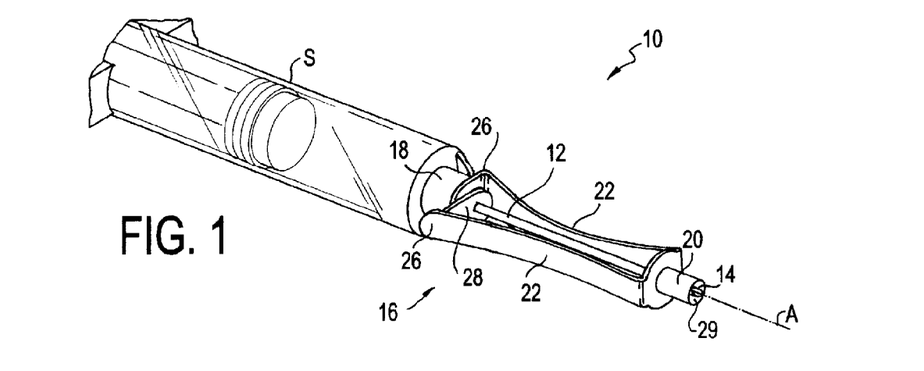
FIG. 1 is a fragmentary perspective view showing a hypodermic syringe employing a first embodiment of the safety needle of the invention.

Referring now in detail to the drawings, there is illustrated in FIG. 1 a hypodermic syringe S employing one embodiment of the safety needle apparatus of the present invention which is designated generally by reference numeral 10. The safety needle 10 comprises a conventional hollow steel hypodermic needle 12 mounted in a support hub 28 and having an axis A and a sharp beveled point or tip 14 for puncturing the skin. The needle 12 and its tip 14 are enclosed in a unitary protective sleeve or sheath 16 having a generally circular cross-section and preferably molded in one-piece of a clear, flexible polymeric material, such as polyethylene, polypropylene or the like. While a circular cross-section of the sheath 16 is preferred, other cross-sectional shapes are possible, including elliptical, rectangular, polygonal and the like.

Sheath 16 comprises a first tubular member or mounting sleeve 18 surrounding the hub 28 and a second tubular member or needle sleeve 20 connected by a plurality (two in this embodiment) of inwardly curved or bowed, but outwardly flexible or bowable ribs or arms 22, which maintain the tubular members 18, 20 in a generally coaxial relationship with one another and with the needle axis A. The inwardly curved or bowed condition of the ribs or arms 22 as shown in FIG. 1 is variously described herein as the "initial" "unstressed" or "at rest" or "safe" state of the ribs or arms. It is to be understood that the terms "initial" "unstressed," "at rest" and "safe" are used herein to describe the initial state, position or condition of the ribs or arms 22 when the safety needle of the invention is removed from its sterile package, as well as the final state, position or condition of the ribs or arms immediately following use of the safety needle when it is ready to be discarded.

Second tubular member or needle sleeve 20 has a passage 24, preferably a central passage, through which the needle 12 can extend in an operative condition of the safety needle. However, in the "at rest" state, the needle sleeve 20 completely surrounds the needle tip 14 and extends axially beyond the tip a distance sufficient to prevent exposure of the tip at the end of the sleeve 20, as more fully explained hereinafter.

Thus, it will be appreciated by those skilled in the art that, in the "at rest" state, the likelihood of an inadvertent needle stick from the needle tip 14 is remote. For instance, if the safety needle was inadvertently pushed axially against a person's body, whether before or after use, the ribs or arms 22 would flex or bow inwardly into contact with the needle 12 and/or each other with no assistance from any additional biasing or restoring element. This will prevent the needle sleeve 20 from moving axially to an extent sufficient to expose the needle tip 14 at the open distal end of the passage 24 in the needle sleeve 20. As will be understood from the foregoing and from the description which follows, this feature of the invention is common to all embodiments.

The ribs or arms 22 are provided at their proximal free ends with operator elements, such as lever-like extensions 26 that are used to operate the safety needle as more fully described in connection with FIGS. 2-17. The operator elements 26 are manually urged toward one another to flex or bow the ribs outwardly and thereby move the needle sleeve 20 proximally toward the mounting sleeve 18. This allows the needle 12 to extend through the central passage 24 of the needle sleeve 20 for administering an injection or the like.

Although only two flexible ribs or arms 22 are shown in the drawings, it should be understood that a greater number of ribs or arms may be used. It is also possible according to the invention to construct the sheath 16 with only a single rib or arm and still achieve the purposes and functions of the invention. Other equivalent arrangements, designs and structures of the inwardly bowed ribs 22 and the sleeves 18, 20 will be apparent to those of skill in the art in light of the teachings herein.

Figure 2:
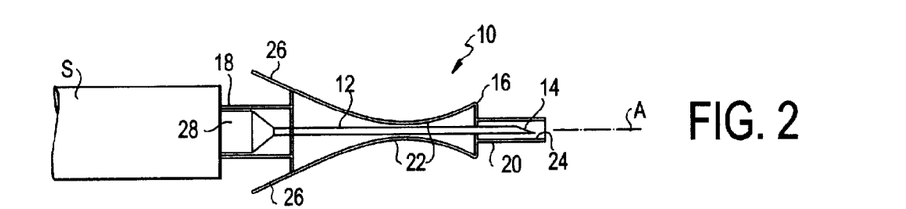
FIG. 2 is a schematic view, in cross-section, illustrating the initial or "at rest" condition of the safety needle of FIG. 1.

Referring now to FIGS. 2-5, there are shown in several schematic cross-sections one operating method sequence for the safety needle of FIG. 1. FIG. 2 schematically illustrates the initial "at rest" state or "safe" condition of the protective sheath 16 of a safety needle apparatus 10 of the present invention, for example, as it would appear having just been removed from a sterile package (not shown). The protective sheath 16 is connected by means of first tubular member or mounting sleeve 18 to the hub 28 of the needle 12. The hub 28, in turn, is connected to the syringe S by means of a collar, leer lock connection or other conventional syringe/needle connection (not shown). Alternatively, the needle 12 may be connected directly to the syringe S, e.g., by a collar (not shown), and the mounting sleeve 18 may be engaged over the collar.

In the initial "at rest" or "safe" state, the tip 14 of the hypodermic needle 12 is disposed completely within the central passage 24 of the second tubular member or needle sleeve 20 and is spaced axially inwardly from the free end thereof so as to prevent needle sticks. The ribs or arms 22 are flexed or bowed inwardly in close proximity to the shaft of needle 12. It is to be understood that, in this "at rest" state or "safe"

condition, the intermediate, radially innermost portions of the ribs 22 may be slightly spaced from the needle 12 as shown in FIG. 2 or may be in contact with the needle 12 and/or each other. The extensions 26 at the proximal ends of the ribs 22 are angled outwardly away from the axis A of the needle 12.

Figure 3:
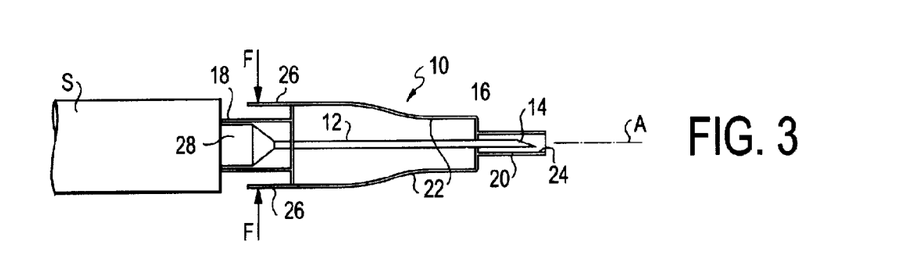
FIG. 3 is a schematic view, in cross-section, illustrating an intermediate condition of the safety needle of FIG. 1 with the arms being initially flexed outwardly.
Figure 4:
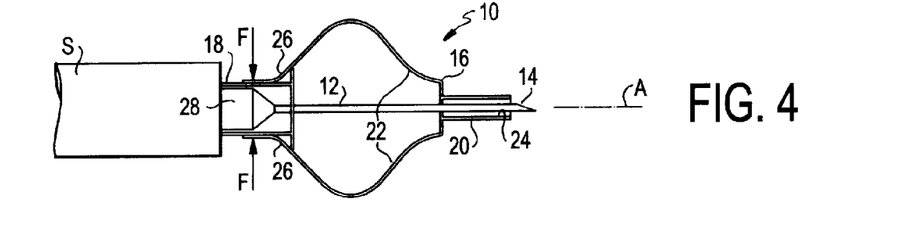
FIG. 4 is a schematic view, in cross-section, illustrating an operative condition of the safety needle of FIG. 1 with the arms bowed outwardly and the needle point exposed beyond the end of the sheath.

FIG. 3 shows an intermediate state of the protective sheath 16 after a force has been applied to both the extensions 26, in this case, radially inward forces F applied manually by the user of the safety needle apparatus 10 to both extensions 26. As shown, the application of the radially inward forces F begins to flex both ribs 22 outwardly away from the needle 12, but the needle tip 14 still remains inside the central passage 24 of the needle sleeve 20. As shown in FIG. 4, continued application of increasing radially inward forces F causes both ribs 22 to flex or bow outwardly, thereby storing energy in the ribs and moving the needle sleeve 20 proximally along axis A to expose the tip 14 of needle 12. In this operative condition, the safety needle apparatus 10 may be used to administer an injection, perform a phlebotomy procedure or the like. During the procedure, the manually applied forces F may be released so that the protective sheath 16 is ready to return to its "at rest" or "safe" condition.

Figure 5:
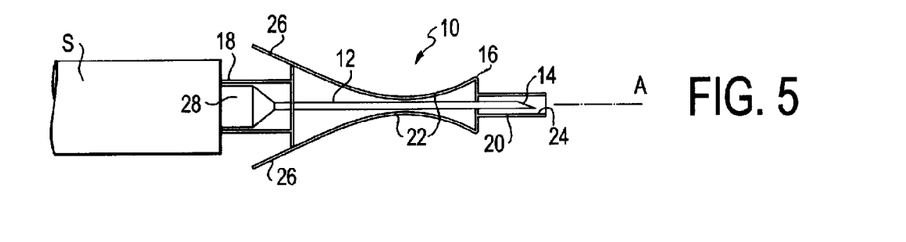
FIG. 5 is a schematic view, in cross-section, illustrating the safety needle of FIG. 1 following an injection with the safety needle returned to its "at rest" or "safe" condition.

After the syringe S and safety needle apparatus 10 have been used, e.g., to administer an injection, and the needle 12 has been withdrawn from the body of a patient, the energy stored in the ribs 22 causes the protective sheath 16 to automatically return to its "at rest" or "safe" state as shown in FIG. 5. No assistance from any additional biasing or restoring means is necessary. In this "safe" state, the tip 14 of the needle 12 is again completely enclosed within the passage 24 of needle sleeve 20 so as to prevent inadvertent needle sticks by the "used" needle.

Figure 6:
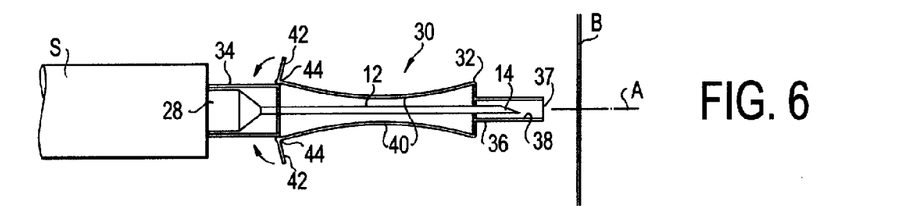
FIG. 6 is a schematic view, in cross-section, illustrating the initial or "at rest" condition of a second embodiment of the safety needle of the invention.

Now referring to FIGS. 6-11, there are shown in several schematic cross-sections a second embodiment of the safety needle of the present invention and an operating method sequence for administering an injection to the body B of a patient. FIG. 6 schematically illustrates the initial "at rest" state or "safe" condition of a protective sheath 32 of a safety needle apparatus 30 of the present invention, for example, as it would appear having just been removed from a sterile package (not shown). The protective sheath 32 is connected by means of first tubular member or mounting sleeve 34 to the hub 28 of the needle 12. In this initial "safe" state, the tip 14 of the hypodermic needle 12 is disposed completely within the central passage 38 of the second tubular member or needle sleeve 36 and is spaced axially inwardly from the open free end 37 thereof so as to prevent needle sticks. The ribs or arms 40 are flexed or bowed inwardly in close proximity to the shaft of needle 12. It is to be understood that, in this "at rest" state or "safe" condition, the intermediate, radially innermost portions of the ribs 40 may be slightly spaced from the needle 12 as shown or may be in contact with the needle 12 and/or with each other. Extensions or levers 42 are affixed, e.g., by integral molding, adhesive bonding, etc., at the proximal ends of the ribs 40 and are angled outwardly from the longitudinal extent of the ribs 40 at an angle of approximately 90°. The levers 42 are designed to be operated by manually rotating them about pivot points 44 in the direction shown by the arrows in FIG. 6. Pivot points 44 may comprise so-called "living hinges," which are well known in the plastic molding arts. Such "living hinges" may be molded between the levers 42 and the mounting sleeve 34.

Figure 7:
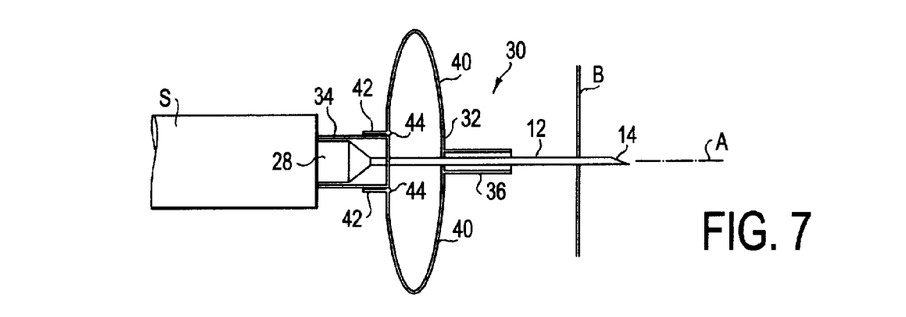
FIG. 7 is a schematic view, in cross-section, illustrating the operative condition of the second embodiment of the safety needle of the invention with the needle penetrating the body of a patient.

FIG. 7 shows the protective sheath 32 after the levers 42 have been manually rotated about pivot points 44 through slightly more than 90° such that the levers lie against the surface of the mounting sleeve 34 and substantially parallel to the needle axis A. The ribs 40 are fully outwardly bowed and the needle tip 14 and needle 12 extend through the central passage 38 of the needle sleeve 36 and into the body B of a patient. The forces applied to the levers 42 to cause the ribs 40 to bow outwardly are stored in the ribs as energy sufficient to return them to the "safe" state as hereinafter described.

Figure 8:
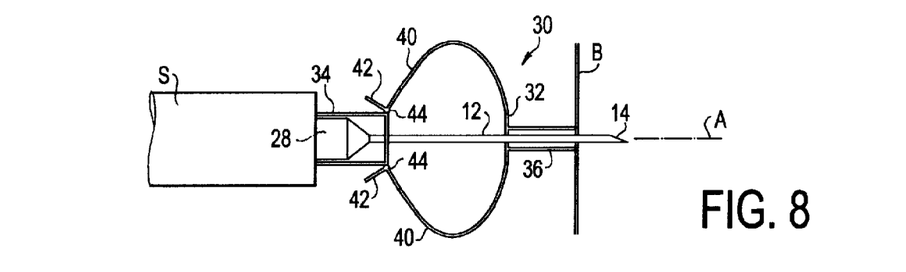
FIG. 8 is a schematic view, in cross-section, illustrating the partial withdrawal of the safety needle of the second embodiment from the body of a patient.
Figure 9:
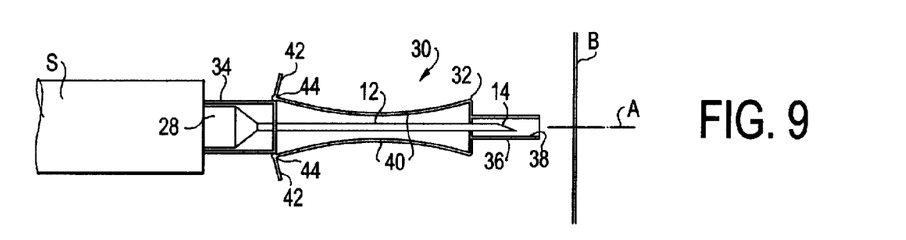
FIG. 9 is a schematic view, in cross-section, illustrating the complete withdrawal of the safety needle of the second embodiment from the body of a patient and the return of the safety needle protective sheath to its "at rest" or "safe" condition.

In FIG. 8, the condition of the protective sheath 32 is shown after the needle 12 has been inserted in the patient's body B and the manual forces applied to both levers 42 by the user have been released. In this condition, the stored energy in the ribs 40 causes them to begin to return to the "at rest" or "safe" state and move the needle sleeve 36 distally into contact with the body B of the patient. After the user has administered the injection, and the needle 12 has been withdrawn from the patient's body B, the remaining energy stored in the ribs 40 causes the protective sheath 32 to automatically return to its "safe" condition as shown in FIG. 9 without the help of any biasing or restoring means. In this "safe" state, the tip 14 of the needle 12 is again completely enclosed within the passage 38 of needle sleeve 36 so as to prevent needle sticks by the "used" needle.

Figure 10:
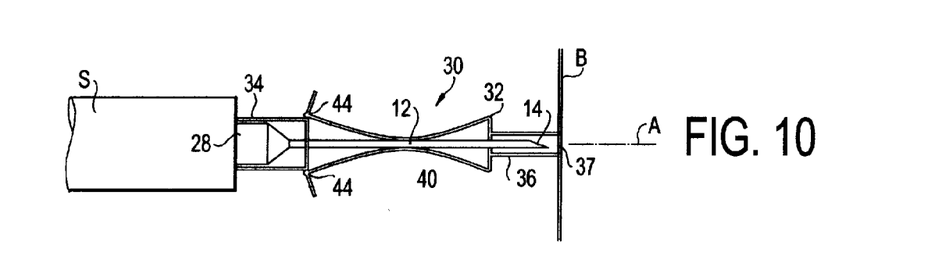
FIG. 10 is a schematic view, in cross-section, illustrating the operation of the safety needle of the second embodiment of the invention when a force is applied to the free end of the protective sheath while the sheath is in the "at rest" condition.

FIG. 10 illustrates what would happen if the open free end 37 of the safety needle apparatus 30, in the initial condition of FIG. 6 or in the "used" condition of FIG. 9, were inadvertently caused to come into contact with any surface, whether that surface is the body B of a patient, the body of a user or any other body or surface. In such case, the ribs 40 bow inwardly into contact with the needle 12 and/or with each other and prevent the needle tip 14 from extending beyond the open free end 37 of the needle sleeve 36 where it might cause a needle stick.

Figure 11:
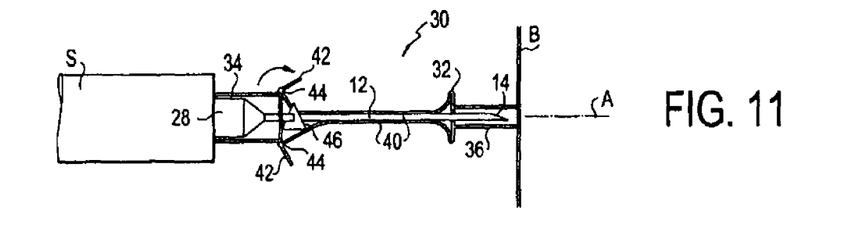
FIG. 11 is a schematic view, in cross-section, illustrating the safety needle of the FIGS. 6-10 second embodiment with a latch to positively lock the protective sheath in a "locked" condition.

FIG. 11 illustrates one modification of the safety needle apparatus of the invention, which may be incorporated in any embodiment of the present invention whether or not it is specifically disclosed herein. The modification comprises an irreversible safety latch 46 that may be molded integrally with the protective sheath 32 or separately affixed thereto. The latch 46 is constructed to engage over the outer surface of one or both of the ribs 40 in their "at rest" or "safe" condition after use so as to positively prevent, reuse of the safety needle or inadvertent operation of the levers 42 to expose the needle tip 14 and cause a needle stick. This condition of the latch 46 and protective sheath 32 is the "locked" condition and is applied only in the "at rest" condition of the safety needle apparatus after it has been used, as shown, for example, in FIG. 9. Following use of the safety needle apparatus, the lever 42 of the locked rib 40 is manually rotated clockwise as shown by the arrow in FIG. 11 so as to permit irreversible engagement of the latch 46.

Figure 12:
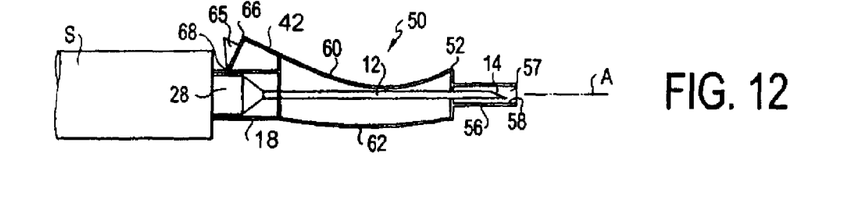
FIG. 12 is a schematic view, in cross-section, illustrating the initial or "at rest" condition of a third embodiment of the safety needle of the invention having both inwardly and outwardly bowed arms.

Referring now to FIGS. 12-16, there is shown, in several schematic cross-sections, a third embodiment of the safety needle apparatus 50 of the invention and an operating method sequence for administering an injection to a patient. In this third embodiment, FIG. 12 schematically illustrates the initial "at rest" state or "safe" condition of a protective sheath 52 of a safety needle apparatus 50 of the present invention, for example, as it would appear having just been removed from a sterile package (not shown). The protective sheath 52 is connected by means of first tubular member or mounting sleeve 18 to the hub 28 of needle 12. In this initial "safe" state, the tip 14 of the hypodermic needle 12 is disposed completely within the central passage 58 of the second tubular member or needle sleeve 56 and is spaced axially inwardly from the open free end 57 thereof so as to prevent needle sticks. The ribs or arms 60, 62 differ from those of the first and second embodiments in that one of the ribs 60 is flexed or bowed inwardly in close proximity to or in contact with the shaft of needle 12 while the other rib 62 is flexed or bowed outwardly away from the shaft of needle 12. An extension or lever 42 is affixed, e.g., by integral molding, adhesive bonding, etc., at the proximal end of the rib 60 and is angled outwardly from the axis A of the needle 12. The lever 42 is designed to be operated by the application of a radially directed, manual force F in the direction shown by the arrow in FIG. 13.

A further feature of the third embodiment, which may be incorporated in any embodiment of the invention whether or not it is disclosed herein, is the provision of a removable or "breakaway" tab 65 (FIG. 12) located between the extension or lever 42 and the mounting sleeve 18. The tab 65 is designed to prevent inadvertent operation of the lever 42 when it is first removed from its package (not shown) and may be incorporated in the safety needle apparatus with or without the safety latch 46 shown in FIG. 11. Preferably, the tab 65 is integrally molded with the protective sheath 52 and provided with weakened points 66, 68 adjacent the lever 42 and the mounting sleeve 18. In order to operate the lever 42, the user must first remove tab 65 by grasping the tab and pulling or twisting it to break it away at the weakened points 66, 68. Once the tab 65 has been removed, the safety needle apparatus may be used as hereinafter described in connection with FIGS. 13-16.

Figure 13:
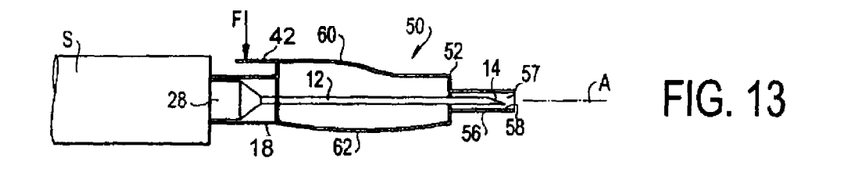
FIG. 13 is a schematic view, in cross-section, illustrating an intermediate condition of the safety needle of the third embodiment of FIG. 12 with the inwardly bowed arm being initially flexed outwardly.
Figure 14:
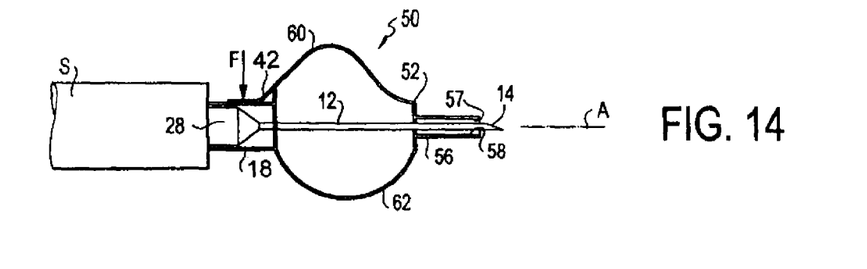
FIG. 14 is a schematic view, in cross-section, illustrating an operative condition of the safety needle of the third embodiment of FIG. 12 with both arms bowed outwardly and the needle point exposed beyond the end of the sheath.
Figure 15:
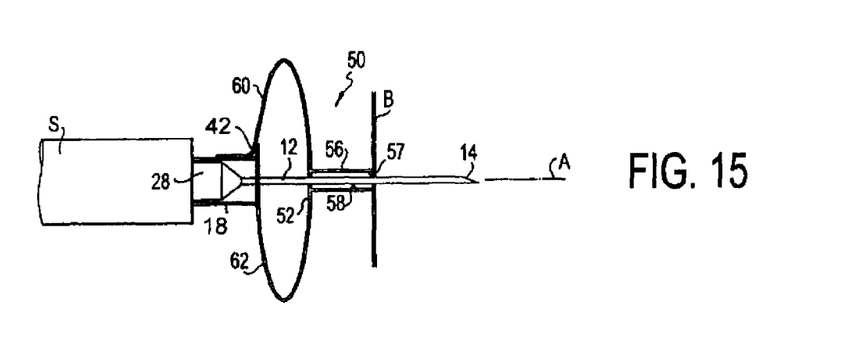
FIG. 15 is a schematic view, in cross-section, illustrating the operative condition of the third embodiment of the safety needle of the invention with the needle penetrating the body of a patient.

FIG. 13 shows an intermediate state of the protective sheath 52 after a force has been applied to the extension or lever 42, in this case, a radially inward force F applied manually by the user of the safety needle apparatus 50 to the lever 42. As shown, the application of the radially inward force F begins to flex rib 60 outwardly away from the needle 12, but the needle tip 14 still remains inside the central passage 58 of the needle sleeve 56. As shown in FIG. 14, continued application of increasing radially inward force F causes rib 60 and the already outwardly bowed rib 62 to flex or bow more outwardly, thereby storing energy in the ribs and moving the needle sleeve 56 proximally along axis A to expose the tip 14 of needle 12. In this operative condition, the safety needle apparatus 50 may be used to perform a phlebotomy procedure or administer an injection to a body B, as particularly shown in FIG. 15. During administration of the injection, it is neither necessary nor desirable to maintain the force on lever 42 because the ribs 60, 62 will remain in their outwardly bowed condition owing to the force applied to the free end 57 of the needle sleeve 56 by the body B of the patient. In addition, after administration of the injection, if the force is maintained on the lever 42, the protective sheath 52 will not return to its "at rest" or "safe" condition upon withdrawal of the needle from the patient's body B.

Figure 16:
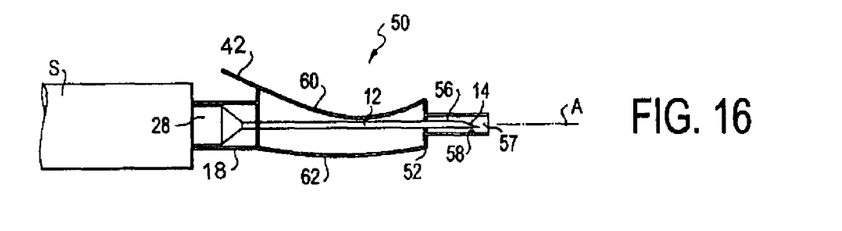
FIG. 16 is a schematic view, in cross-section, illustrating the complete withdrawal of the safety needle of the third embodiment from the body of a patient and the return of the safety needle protective sheath to the "at rest" or "safe" condition.

After the syringe S and safety needle apparatus 50 have been used to administer the injection, and the needle 12 has been withdrawn from the body of the patient, the energy stored in the ribs 60, 62 causes the protective sheath 56 to automatically return to its "at rest" or "safe" state as shown in FIG. 16 without the aid of any additional biasing or restoring means. In this "safe" state, the tip 14 of the needle 12 is again completely enclosed within the passage 58 of needle sleeve 56 so as to prevent inadvertent needle sticks by the "used" needle.

Figure 17:
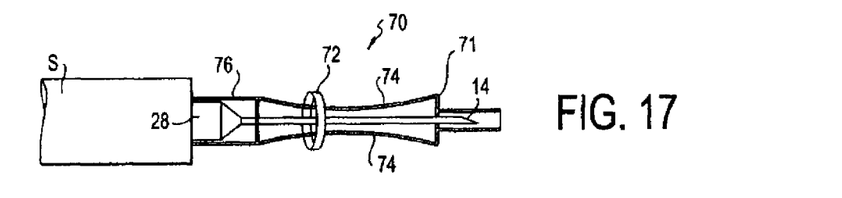
FIG. 17 is a schematic view, in cross-section, illustrating the initial or "at rest" condition of a fourth embodiment of the safety needle of the invention.

FIG. 17 illustrates another embodiment of the safety needle apparatus 70 of the invention with a protective sheath 71 in the "at rest" or "safe" condition. In this embodiment, the lever means for operating the ribs to flex outwardly comprises a curved member or circular loop 72 spanning the ribs 74 adjacent the mounting sleeve 76. A radially inward manual force applied to the loop 72 causes the ribs to flex or bow outwardly into an operative condition. After use of the safety needle 70, the energy stored in the ribs 74 will return the protective sheath 71 to its "at rest" or "safe" condition without the help of any additional biasing or restoring means.

Figure 18:
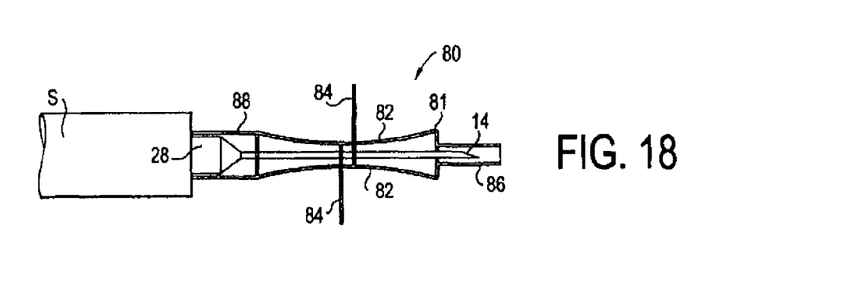
FIG. 18 is a schematic view, in cross-section, illustrating the initial or "at rest" condition of a fifth embodiment of the safety needle of the invention.

FIG. 18 illustrates another embodiment of the safety needle apparatus 80 of the invention with a protective sheath 81 in the "at rest" or "safe" condition. In this embodiment, the lever means for operating the ribs 82 to flex outwardly comprises a pair of pusher members or rods 84 attached to and extending across the ribs 82 intermediate the mounting sleeve 88 and the needle sleeve 86. Oppositely directed manual forces applied to the free ends of the pusher members 84 cause the ribs 82 to flex or bow outwardly into an operative condition. After use of the safety needle 80, the energy stored in the ribs 82 will return the protective sheath 81 to its "at rest" or "safe" condition without the help of any additional biasing or restoring means.

It will be appreciated by those of skill in the art that it would be possible to construct any of the disclosed embodiments of the invention with only one inwardly bowed rib rather than a plurality of ribs. It will also be appreciated that other forms of the levers, latch and breakaway tab means may be used to operate the ribs and to irreversibly lock or latch the ribs in their used "at rest" conditions.

Although a certain presently preferred embodiment of the invention has been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A safety needle for insertion into the body of a patient comprising a hypodermic needle having a needle axis and a needle point and being mounted in a needle support, a protective sheath having an axis and comprising a mounting sleeve for mounting said sheath to the needle support, a needle sleeve with an open distal end for housing said needle point and a passage through which the needle is adapted to pass, and flexible means for supporting said needle sleeve from said mounting sleeve, said flexible means comprising at least one rib having two ends, said rib being connected at one end to said mounting sleeve and at the other end to said needle sleeve, said rib having an unflexed, at rest condition and a flexed condition such that in the unflexed condition the rib is bowed inwardly toward said needle and in the flexed position the rib is bowed outwardly away from the needle, said rib being automatically movable from the flexed condition to the unflexed condition when the needle is withdrawn from the body of the patient so as to automatically position the needle point within the needle sleeve without the assistance of any additional biasing or restoring means.

2. The safety needle of claim 1, including a plurality of said ribs having the same length.

3. The safety needle of claim 1, including a second rib having two ends, said second rib being connected at one end to said mounting sleeve and at the other end to said needle sleeve, said rib having an unflexed, at rest condition and a flexed condition such that in both the unflexed and flexed conditions the second rib is bowed outwardly away from said needle.

4. The safety needle of claim 1, including means attached to said rib for urging said rib from its unflexed condition toward its flexed condition.

5. The safety needle of claim 4, wherein said urging means comprises an extension of said rib.

6. The safety needle of claim 4, wherein said urging means comprises a lever extending at an angle to said rib, said lever having a pivot point adjacent said mounting sleeve.

7. The safety needle of claim 1, including latch means for irreversibly locking said rib in its unflexed condition only after use of the safety needle.

8. The safety needle of claim 1, including a removable tab means for locking said rib in its unflexed condition only before use of the safety needle.

9. The safety needle of claim 8, wherein said removable tab means comprises a tab with connections to said mounting sleeve and said rib, the connections including weakened points adapted to be broken by a user of the safety needle.

10. The safety needle of claim 1, wherein said protective sheath is molded in one piece of a polymeric material.

11. A safety needle for insertion into the body of a patient comprising a hypodermic needle having a needle axis and a needle point and being mounted in a needle support, a protective sheath having an axis and comprising a mounting sleeve for mounting said sheath to the needle support, a needle sleeve with an open distal end for housing said needle point and a passage through which the needle is adapted to pass, and flexible means for supporting said needle sleeve from said mounting sleeve, said flexible means comprising a plurality of ribs each having two ends, each rib being connected at one end to said mounting sleeve and at the other end to said needle sleeve, said ribs having an unflexed, at rest condition and a flexed condition such that in the unflexed condition the ribs are bowed inwardly toward said needle and in the flexed position the ribs are bowed outwardly away from the needle, a lever attached to each rib for moving said rib from its unflexed condition toward its flexed condition, said ribs being automatically movable from the flexed condition to the unflexed condition when the needle is withdrawn from the body of the patient so as to automatically position the needle point within the needle sleeve without the assistance of any additional biasing or restoring means.

12. A method of using a safety needle comprising a hypodermic needle having a needle axis and a needle point and being mounted in a needle support, a protective sheath having an axis and comprising a mounting sleeve for mounting said sheath to the needle support, a needle sleeve with an open distal end for housing said needle point and a passage through which the needle is adapted to pass, and flexible means for supporting said needle sleeve from said mounting sleeve, said flexible means comprising at least one rib having two ends, said rib being connected at one end to said mounting sleeve and at the other end to said needle sleeve, said rib having an unflexed, at rest condition and a flexed condition such that in the unflexed condition the rib is bowed inwardly toward said needle and in the flexed position the rib is bowed outwardly away from the needle, a lever attached to the rib for moving said rib from its unflexed condition toward its flexed condition, said method comprising the steps of:

applying a force to said lever to move said rib from its inwardly bowed, unflexed condition toward its outwardly bowed, flexed condition and extend the needle point through the open distal end of the needle sleeve;

inserting the needle into the body of a patient;

releasing the force on said lever; and removing the needle from the body of the patient and the needle sleeve away from contact with the body of the patient to permit the rib to automatically return to its unflexed, at rest condition with the needle point enclosed within the needle sleeve without the assistance of any additional biasing or restoring means.

* * * * *